United States Patent
Levy

(10) Patent No.: US 6,630,106 B1
(45) Date of Patent: Oct. 7, 2003

(54) COMPOSITIONS AND METHODS FOR CONTROLLING MICROORGANISM GROWTH IN WATER PROCESSING SYSTEMS

(75) Inventor: Ehud Levy, Roswell, GA (US)

(73) Assignee: Selecto, Inc., Suwanee, GA (US)

( * ) Notice: Subject to any disclaimer, the term of this patent is extended or adjusted under 35 U.S.C. 154(b) by 0 days.

(21) Appl. No.: 09/805,758

(22) Filed: Mar. 13, 2001

(51) Int. Cl.$^7$ ................................ A61L 2/23; C02F 1/50
(52) U.S. Cl. .................... 422/28; 210/757; 210/758; 210/763; 210/764; 424/489; 424/635
(58) Field of Search ................ 422/28; 210/748, 210/757, 758, 763, 764; 424/421, 489, 632; 62/3.2

(56) References Cited

U.S. PATENT DOCUMENTS

| | | | | |
|---|---|---|---|---|
| 4,092,245 A | * | 5/1978 | Franks et al. ................. | 210/64 |
| 4,238,334 A | | 12/1980 | Halbfoster .................... | 210/679 |
| 4,263,266 A | | 4/1981 | Michel et al. ................ | 423/329 |
| 4,377,555 A | | 3/1983 | Hancock et al. .............. | 252/430 |
| 4,496,528 A | | 1/1985 | Bourgogne et al. ........... | 502/60 |
| 4,767,733 A | | 8/1988 | Chester et al. ............... | 502/65 |
| 4,891,949 A | * | 1/1990 | Caldarola ...................... | 62/3.2 |
| 4,994,249 A | | 2/1991 | Verduijn ...................... | 423/328 |
| 4,995,975 A | | 2/1991 | Jacquot et al. .............. | 210/266 |
| 5,073,272 A | | 12/1991 | O'Neil ......................... | 210/728 |
| 5,078,978 A | | 1/1992 | Talbet et al. ................. | 210/912 |
| 5,118,655 A | | 6/1992 | Pederson ...................... | 502/412 |
| 5,133,871 A | | 7/1992 | Levy ............................ | 210/688 |
| 5,175,110 A | | 12/1992 | Bradshaw et al. ........... | 210/662 |
| 5,236,680 A | | 8/1993 | Nakazawa et al. ............ | 502/68 |
| 5,238,676 A | | 8/1993 | Roth et al. ................... | 502/64 |
| 5,346,924 A | * | 9/1994 | Giuffrida ..................... | 521/28 |
| 5,401,416 A | | 3/1995 | Levy ............................ | 210/668 |
| 5,460,734 A | | 10/1995 | Birbara et al. .............. | 210/763 |
| 5,503,840 A | * | 4/1996 | Jacobson et al. ............ | 424/421 |
| 5,538,746 A | | 7/1996 | Levy ............................ | 426/477 |
| 5,552,058 A | * | 9/1996 | Fanning ...................... | 210/469 |
| 5,562,941 A | | 10/1996 | Levy ............................ | 426/433 |
| 5,587,089 A | * | 12/1996 | Vogel et al. ................. | 210/164 |
| 5,612,522 A | | 3/1997 | Levy ........................... | 204/157.4 |
| 5,616,243 A | | 4/1997 | Levy ............................ | 210/282 |
| 5,645,727 A | | 7/1997 | Bhave et al. ................ | 210/651 |
| 5,655,212 A | | 8/1997 | Sekhar et al. ................ | 428/552 |
| 5,681,475 A | | 10/1997 | Lamensdorf et al. ........ | 210/660 |
| 5,737,932 A | * | 4/1998 | Lee ............................. | 62/135 |
| 5,868,924 A | * | 2/1999 | Nachtman et al. ........... | 210/85 |
| 5,879,565 A | * | 3/1999 | Kusmierz et al. ........... | 210/757 |
| 5,915,851 A | * | 6/1999 | Wattrick et al. .............. | 4/619 |
| 5,961,843 A | * | 10/1999 | Hayakawa et al. ......... | 210/748 |
| 6,039,891 A | * | 3/2000 | Kaufman et al. ........... | 252/79.1 |
| 6,200,483 B1 | | 3/2001 | Cutler et al. ................ | 210/685 |
| 6,241,893 B1 | | 6/2001 | Levy ............................ | 210/660 |

FOREIGN PATENT DOCUMENTS

| | | | |
|---|---|---|---|
| EP | 0 515 936 A1 | 12/1992 | ........... B01D/71/02 |
| JP | 02290291 A | * 11/1990 | |
| JP | 11207359 A | * 8/1999 | |
| WO | 96 06814 A | 3/1996 | |

* cited by examiner

Primary Examiner—Robert J. Warden, Sr.
Assistant Examiner—Sean E. Conley
(74) Attorney, Agent, or Firm—Kilpatrick Stockson LLP; John S. Prutt; Bruce D. Gray

(57) ABSTRACT

The invention relates to methods and compositions for reducing the growth of microorganisms and other contaminants of water processing and holding systems. Rapid reduction in the growth of fungi, algae, spores, molds, bacteria, protozoa and/or other contaminating microorganisms found in water processing and holding equipment is achieved by placing a material comprising an antimicrobial composition, preferably one containing a metal oxide and a binder, in an area of such equipment where there is water movement or storage, thereby destroying contaminating water-borne or air borne microorganisms in the water and on the surfaces of the equipment in contact with the water.

32 Claims, No Drawings

COMPOSITIONS AND METHODS FOR CONTROLLING MICROORGANISM GROWTH IN WATER PROCESSING SYSTEMS

BACKGROUND

1. Field of the Invention

This invention relates to compositions and methods for controlling the growth of microorganisms and other contaminants in water processing systems, including, but not limited to, ice makers, water coolers, refrigerators, water filtration devices, cooling towers and water reservoirs. The compositions and methods of the present invention reduce the presence and/or inhibit the growth of microorganisms, such as fungi, algae, spores, molds, mildews, protozoa, bacteria and other contaminants of water processing systems. The composition contains a solid metal oxide which is at least partially immersed in a reservoir of the water recirculation system.

2. Description of the Related Art

Equipment used to process and store water often supports heavy growth of microbiological contaminants, such as bacteria, fungi, algae, spores, molds, mildews, and an assortment of other microorganisms. The presence of such contaminants in significant quantities is undesirable and creates unhealthy conditions in equipment used to process water for everyday use or consumption by humans, raising potential health code violations. Moreover, in equipment for processing non-potable water, such as cooling towers and water chillers used in cooling systems, overgrowth of contaminants can lead to fouling of process equipment, causing decreased efficiency and corrosion.

The site and identity of the contaminating growth may depend upon the particular chemistry of the water in the system, as well as upon the contents of the air near the water processing system. For instance, ice makers and water coolers located in bakeries, delis and other establishments having bread-making and other baking operations often suffer from heavy microbial growth covering up to 80% of the surface area of the equipment possibly due to the high quantities of airborne yeast in these environments which can get transported into the water processing system. It has also been noted that ice makers and water coolers located near copy machines tend to suffer from increased microbial growth. This is believed to be related to the presence of volatile organic substances used in the copying process and which are carried through the air to the water systems and provide nutrients the microbes.

Although attempts have been made to deal with the problem of overgrowth of such contaminants in water processing and holding systems, no successful remedy has been discovered. A traditional treatment for water contamination involves sterilizing the water with chemicals before it enters the processing equipment. This method has proven unsuccessful, because the contaminants generally grow on the surfaces of the equipment itself; thus, the sterilized water becomes contaminated again when it enters the process equipment. Cleaning the water prior to putting it into a contaminated system thus does not significantly reduce the contamination of the water output. Additionally, the sterilized water does little to reduce the microbial build up already present in the system since the level of any antimicrobials in the water is generally not sufficient to reduce or destroy an established microbe infection in the equipment. The equipment can be disinfected prior to addition of the treated water; however, the cleaning process generally requires shutting down the system for long periods of time during the cleaning. Also, many contaminants are airborne and, as such, may enter the equipment after the pre-treated water has been added, and after cleaning has occurred.

Other prior art treatments include the use of chlorine as a disinfectant. Chlorination disinfects the water and equipment, but it also causes the equipment to corrode. In ice makers, the chlorine in the water becomes incorporated into the ice, giving an unpleasant taste and odor to the ice. Attempts have also been made, primarily in Japan, to decontaminate the water with magnesium pellets and ammonia. Although this method cleanses the water of contaminants, use of these chemicals in drinking water in the United States is not yet authorized by the EPA.

Ultra violet lamps have also been placed in or near the reservoirs of water systems to generate ozone, which poisons the microorganisms. However, this method also has not proven capable of efficiently reducing the growth of contaminants for a sustained period of, time. Additionally, this technique does not appear to work well at low temperatures, which makes it an impractical solution to microbial overgrowth in water coolers, refrigerators, ice makers, chillers, and other water processing equipment affected by this problem. Finally, this technique requires the consumption of additional electrical power.

A common problem with all of the above techniques is that while they achieve partial reduction of some microorganisms, they do not have a wide effectiveness; i.e. they typically cannot both reduce bacterial contamination and also control the growth of spores, fungus and algae for more than a short period of time.

Another prior art technique involves impregnating plastic with biocides and using the treated plastic to form the reservoir and/or other parts of water processing equipment that suffer from microbial growth. This method has proven relatively ineffective at reducing microbial growth to a sufficiently low level of detection. Making the impregnated plastic also involves increased costs associated with customized production of the parts for each different system or application. This method presents an additional problem in that the parts are not easy to obtain or replace. As with all of the above-described prior art disinfecting techniques, this method is only mildly successful in reducing the growth of microorganisms. Over a period of time, new growth of microorganisms will become sufficiently well established that the colonies of organisms will become visible to casual inspection of the surface of the equipment.

Thus, what is needed in the art are methods and compositions for quickly and effectively reducing or eliminating the growth of various microorganisms in water processing equipment and holding tanks and maintaining the reduced-microbial environment for sustained periods of time. Preferably, the method should also be convenient and cost-effective.

SUMMARY OF THE INVENTION

The invention relates to methods and compositions for reducing the growth of microorganisms and other contaminants of water processing and holding systems. As used herein the term "microorganisms" refers to any microscopic organism, including but not limited to algae, fungi, bacteria, protozoa, mold, mildew, and spores.

In its broad aspects, the invention relates to placing an antimicrobial material in any area of water processing, cooling or holding equipment where there is water movement or water storage. More particularly, the antimicrobial material is placed in a water reservoir or holding or overflow tank of such equipment. Placing the antimicrobial material in the water reservoir, where it is at least partially immersed in the water, destroys contaminating microorganisms in the water and on the surfaces of the equipment in contact with the water. Water-borne or air-borne microorganisms that subsequently contact the antimicrobial material are also killed. When placed in water processing equipment, such as an ice maker, water filtration device, or water recirculation apparatus, placing the antimicrobial material in the water reservoir reduces the presence of the contaminants in the entire system.

The invention provides methods and compositions for significantly reducing the growth of undesirable contaminants in water processing and holding equipment. The invention further provides methods and compositions which work quickly and require little expense or maintenance.

In a particular embodiment, the antimicrobial material of the invention comprises a powdered or fumed metal oxide. The metal oxide can be formed into a shaped solid, or into granules, pellets, extrudates, or other solid forms. The metal oxide may include, but is not limited to, oxides of titanium, silver, copper, zinc and zirconium, or combinations thereof.

In one embodiment, the antimicrobial material comprises at least titanium dioxide, especially fumed titanium dioxide. The titanium dioxide, whether fumed or granular or in some other form, may be optionally combined with other oxides, such as copper oxide, zinc oxide, or both.

The metal oxide or oxides may be blended with an additional material or substrate, typically an inorganic material such as alumina, silica, or carbon powder and with a binder, such as a high-density polyethylene binder. The metal oxide mixture may then be heated and compressed to form a solid shape, such as a block, for placement in a water reservoir.

Particularly in applications where the water in the reservoir is known or believed to contain quantities of $H_2S$, the metal oxide material in the reservoir may be complemented by inclusion in the reservoir (at least partially immersed in the water) of a metallic composition comprising copper metal, zinc metal or an alloy of zinc or copper or both. The metallic composition may be added in the form of wires or a powder. In a particular embodiment the metallic composition is in the form of a wool of metal wire or filaments made from an alloy of zinc and copper.

The methods and compositions of the invention work quickly and efficiently, and have been demonstrated to reduce fungus, algae, spore, and bacterial buildup in ice machines by at least 99% within a few hours. The methods and compositions provided successfully reduce the growth of unwanted microbes and other contaminants in both hard and soft water and at a wide range of temperatures, from about 34° to about 100° F., for an unlimited period of time. In particular, the compositions and methods of the invention work very well at low temperatures in the range of about 34° to about 38° F. and particularly demonstrate excellent performance at temperatures of about 36° to about 38° F., which makes the invention particularly advantageous for use in water cooling equipment and ice makers.

Use of the methods and compositions of the invention in water coolers and ice makers in the restaurant business, which represents approximately 99% of the world-market for such equipment, will reduce the exposure of consumers to microorganisms and other contaminants. This will significantly decrease a significant health risk as well as reduce the incidence of penalties and fees imposed by regulatory agencies.

These and further advantages of the present invention will become apparent after a review of the following detailed description of the disclosed embodiments.

DETAILED DESCRIPTION OF SPECIFIC EMBODIMENTS

The invention can be more clearly understood by referring to the following detailed description and specific examples. Although various changes and modifications within the spirit and scope of the invention will become apparent to those skilled in the art from reading this description, the description and examples are presented as illustrations and not intended to limit the scope of the invention in any way.

The invention rapidly reduces the growth of fungi, algae, spores, molds, bacteria, protozoa and/or other contaminating microorganisms in water processing and holding equipment. The method of reducing the unwanted microbial growth comprises placing a material comprising an antimicrobial composition in an area of such equipment where the water can contact and at least partially immerse the composition, e.g., areas where there is water movement or storage. As an example, the antimicrobial material may be placed in a water reservoir of the system. For instance, in an ice maker, the antimicrobial material can be placed in the area of the water reservoir near the water pump or other recirculation mechanism.

As discussed above, in one embodiment of the invention, the antimicrobial material contains a metal oxide. The presence of the metal oxide in the water is believed to result in a catalytic reaction which significantly reduces the growth of microorganisms. Appropriate metal oxides for use in the present invention include, but are not limited to, oxides of titanium, silver, copper, zinc and zirconium, or combinations thereof. In a particular embodiment, the antimicrobial material contains titanium dioxide, which may optionally be combined with copper oxide, zinc oxide, or both. While not wishing to be bound to any particular theory, it is believed that combining the titanium dioxide with zinc oxide and/or copper oxide provides enhanced antimicrobial activity because the titanium dioxide is particularly effective against bacterial contaminants, such as *E. coli*, while the zinc and copper oxides appear to be especially helpful in eliminating fungi and algae.

The metal oxide in the antimicrobial material of the invention may be powdered, granulated, or fumed. As used herein, "fumed" refers to particles ranging in size from about 20 nm to about 100 microns, more particularly from about 20 nm to about 25 microns, even more particularly from about 20 nm to about 100 nm. Fumed metal oxides have been found to be particularly suitable for this invention. In particular, fumed titanium dioxide, alone or combined with fumed copper oxide and/or fumed zinc oxide, has been found to work well. The granulated, fumed or powdered metal oxides may be formed into a compressed shape or block, granules, pellets, extrudate, or any other solid form capable of placement in a water reservoir. Alternatively the powdered or fumed metal oxides may be applied to or coated on a plastic shape, such as a honeycomb, capable of being at least partially immersed in the water in the reservoir. Such a shape should provide additional surface area for water to contact the metal oxide without significantly reducing the flow of water through the reservoir.

The metal oxide may optionally be combined with a substrate of alumina, silica or carbon powder. The metal oxide or metal oxide blended with alumina, silica or carbon powder may be additionally combined with a binder, such as high density polyethylene binder. For instance, an antimicrobial material of the present invention may comprise from about 2 to about 75 weight percent of metal oxide, from about 10 to about 25 weight percent of binder and from about 10 to about 70 weight percent of a substrate such as carbon powder, alumina silicate, or other silicate. The metal oxide portion of the material may contain titanium dioxide, or it may comprise from about 30% to about 90% of titanium dioxide and between about 10% and about 70% of copper oxide, zinc oxide or a combination of both. The portion of copper oxide and zinc oxide may contain these compounds in any ratio. Desirably, the copper oxide and zinc oxide are present in equal amounts (based on wt %).

In one embodiment approximately 22% wt of $TiO_2$, 1.5 wt % of CuO, 1.5 wt % of ZnO was combined with 52 wt % of alumina, silica or carbon powder and blended with 23 wt % of a high density polyethylene binder. In another embodiment, 5% wt of $TiO_2$, 2.5 wt % of CuO, 7.5 wt % of ZnO was combined with 65 wt % of alumina, silica or carbon powder and blended with 20 wt % of a high density polyethylene binder. The compositions of the invention can be formed into a porous block by mixing and heating in a mold until the binder becomes flowable. This block can then be simply introduced into, e.g., the water reservoir of an ice maker, where it will operate to keep the surfaces of the icemaker virtually free from microbial growth.

For example, the compositions described above may be heated to high temperatures, from approximately 280° to approximately 65°, preferably from about 350° to about 400° F., for approximately 1.5 to 3 hours to melt the binder, followed by compression and cooling to form a hydrophilic solid material with a strong surface attraction for microorganisms, such as the porous block described above.

In one embodiment the metal oxide composition is heated to extremely high temperatures, from about 700° to about 1100° C., sufficient to cause the binder to decompose, resulting in a porous, more hydrophilic solid, which provides increased surface area for the contaminants in the water to contact the metal oxide.

The composition may also be formed into pellets or granules, e.g., by extruding the mixture and chopping or grading the extrudate.

In yet another embodiment, the metal oxide composition may be combined with a metallic material comprising copper metal, zinc metal or an alloy of zinc or copper or both. The metallic composition may be in any form. Wires or powders have been found to be suitable. In a particular embodiment, a metallic wire made out of an alloy of zinc and copper is used. The metal wire can be in the form of a metal "wool" that can be at least partially immersed in the water of the reservoir to be treated. In a particular embodiment, the metal oxide is titanium dioxide, and a metal wool is used that contains zinc and copper, in a zinc to copper ratio ranging between about 70:30 and about 50:50. The combination of the metal oxide with the metal wool significantly reduces the concentration of bacteria, mold and yeast in water systems and is particularly useful when the water contains hydrogen sulfide. This is believed to result from redox reactions which occur in the presence of hydrogen sulfide.

The metal oxide compositions described above successfully reduce the growth of unwanted microbes and other contaminants in both hard and soft water and at a wide range of pH levels and temperatures for significant periods of time. The compositions and methods of the invention exhibit maximum efficiency at a pH range between about 5.5 and about 8.5. The invention effectively reduces microbial growth at temperatures from about 34° to about 100° F., more particularly from about 34° to about 85° F. These compositions and methods also work very well at low temperatures in the range of about 34° to about 38° F. and particularly demonstrate excellent performance at temperatures of about 36° to about 38° F., a significant advantage for disinfecting water cooling equipment and ice makers.

The antimicrobial material of the present invention is used in such amounts as necessary to effectively reduce the level of microbial growth in the water system. The surface area of the material may represent between 2 and 10% of the total surface area of the reservoir of the system, but this range is not meant to be limiting and much smaller or larger amounts may be employed as necessary for each particular system. A particular advantage of the present invention is that very small amounts of the antimicrobial material may be effective at virtually eliminating all contaminating growth within a matter of hours, as is demonstrated in the examples below. For instance, the metal oxide may be present in amounts ranging from about 2% to about 75%, more particularly from about 14% to about 30%.

EXAMPLES

Example 1

1000 CC of water were being recirculated at a rate of 0.2 gallons per minute. 0.007 grams of a metal oxide composition containing 90% wt of fumed zinc oxide and 10% wt of fumed titanium dioxide was added to the water. In dry form, the metal oxide particles, agglomerated with high density polyethylene, had a mean particle size of about 40 μm. 30,000 CFU of *E. Coli* per ml of water were introduced into the-beaker. After 1.0 hour the *E. Coli* had been reduced by 99.9%, and after another 1.5 hour had been further reduced to 99.99%. After 2 hours, a 99.999% reduction of *E. Coli* was obtained. After a total of 4 hours, the *E. Coli* had been reduced by 99.9999%.

Example 2

The procedure of Example 1 was repeated with 26,000 CFU of *S. Aures* per ml of water. After 1 hour a 99.9% reduction of bacteria was observed, while at 2 hours the *S. Aures* had been further reduced to 99.99%. At the end of 4 hours the S. Aures had been reduced by 99.999%.

Example 3

The procedure of Example 1 was repeated with 20,000 CFU of *K. Pneumonia* per ml of water. After 1 hour the *K. Pneumonia* had been reduced by 99.99%, and at the end of 4 hours the it had been reduced by 99.999%.

Example 4

4.2 gallons of water were being recirculated in a tank at a rate of 0.2 gallons per minute. 0.007 grams of a metal oxide composition containing 90% wt of fumed titanium dioxide and 7% wt of fumed copper oxide was added to the tank (water of hydration made up the other 3% of the metal oxide composition). The metal oxide particles had a mean particle size of about 25 μm. Bacterial colonies were introduced into the beaker as indicated in Table 1 below. Three trials were run, each with a different bacterial strain. The system was observed and the amount of bacteria was measured at time intervals of 0.5 to 1 hour. The results appear in Table 1 below, which shows the percent reduction of the bacteria over time.

TABLE 1

| TIME | E. Coli (30,000 CFU/CC) | S. Aures (26,000 CFU/CC) | K. Pneumoniae (20,000 CFU/CC) |
|---|---|---|---|
| 1 hour | 99.9% | 99.9% | 99.99% |
| 1.5 hours | 99.99% | | |
| 2 hours | 99.999% | 99.99% | |
| 4 hours | 99.9999% | 99.999% | 99.999% |

Example 5

An antimicrobial composition was made by combining 5% wt fumed $TiO_2$, 2.7% wt. CuO, 7.5% wt ZnO, 20% wt high density polyethylene and 65% wt alumina. The mixture was then heated to 350°–400° F. for a period of 1.5 hours. After heating the composition was compressed and cooled to form a solid block. The block was hydrophilic, having pores ranging from 1–20 $\mu$.

Example 6

The antimicrobial block composition made according to example 5 were field tested in ice machines located inside bakeries. The block was positioned in the water reservoir of the ice machines. The microbial buildup in the ice machines was reduced by 99% within one hour.

Example 7

An antimicrobial composition was made by combining 25 wt % of a metal oxide mixture with 23% wt of high density polyethylene binder and 52% wt of carbon powder. The metal oxide mixture contained about 90% wt of $TiO_2$ and about 10% wt of a 50:50 ZnO, CuO mix (thus, the $TiO_2$ made up about 22.5% wt of the total mixture and the ZnO and CuO mix made up about 2.5%wt of the total mixture). The mixture was then heated to about 350° to about 600° F. to melt the binder. The composition was then cooled and compressed into a block.

Example 8

The composition according to example 7 was tested for antimicrobial activity. A 50 gram block of the composition from Example 7 was placed in a 6"×6"×24"plastic ice machine reservoir tank, in which 3.6 gallons of water was circulated by a recirculation pump at a rate of 0.2 gallons per minute. 5000 CFU of E. Coli per ml of water were introduced into the tank. After 60 minutes there was a 99% reduction of E. Coli. After 12 hours the reduction was maintained at 99%. At 24 and 48 hours the E. Coli had been reduced by 99.999%.

Example 9

A 6"×6"×24"plastic tank impregnated with 3.3% Microban® Biocide Media for Plastic was obtained. This tank was also filled with 3.6 gallons of recirculating water, being pumped at a rate of 0.2 gallons per minute. The tank also contained,5000 CFI of E. Coli, per ml of water. After 60 minutes and 12 hours no reduction of E. Coli was observed. At 24 hours there was a 24% reduction of E. Coli. At 48 hours the E. Coli had been reduced by 40%. Some of this later reduction is also believed to be a result of the natural death of the; colony due to the temperature and the light conditions of the system.

What is claimed is:

1. A method of reducing the growth of microorganisms in water processing or storage equipment comprising at least partially immersing a material comprising an antimicrobial composition in the water in a vessel or conduit inside the equipment, wherein the antimicrobial composition comprises an antimicrobial-effective amount of at least one fumed metal oxide selected from the group consisting of titanium dioxide, copper oxide, zirconia, zinc oxide, silver oxide, and mixtures thereof, and a binder, and wherein at least a portion of the metal oxide is in contact with the water.

2. The method of claim 1, wherein the vessel or conduit is a water reservoir or overflow tank.

3. The method of claim 2, wherein the material is at least partially immersed in the vicinity of a water pump or other circulation device.

4. The method of claim 1, wherein the water processing equipment comprises an ice maker.

5. The method of claim 1, wherein the water processing equipment comprises a water cooler.

6. The method of claim 1, wherein the water processing equipment comprises a refrigerator.

7. The method of claim 1, wherein the water processing equipment comprises a water filtration apparatus.

8. The method of claim 1, wherein the water processing equipment comprises a reverse osmosis unit.

9. The method of claim 8, wherein the vessel or conduit comprises one or more bladder tanks.

10. The method of claim 1, wherein the water processing equipment comprises a cooling tower.

11. The method of claim 1, wherein the water processing equipment comprises a chiller.

12. The method of claim 1, wherein the metal oxide comprises titanium dioxide.

13. The method of claim 12, wherein the metal oxide further comprises copper oxide.

14. The method of claim 12, wherein the metal oxide further comprises zinc oxide.

15. The method of claim 12, wherein the metal oxide further comprises copper oxide and zinc oxide.

16. The method of claim 1, wherein the material further comprises a substrate selected from the group consisting of carbon, alumina, and silicates.

17. The method of claim 1, wherein the binder comprises high density polyethylene.

18. A method of reducing the growth of microorganisms in water processing or storage equipment comprising at least partially immersing a material comprising an antimicrobial composition in the water in a vessel or conduit inside the equipment, wherein the antimicrobial composition comprises an antimicrobial-effective amount of at least one metal oxide selected from the group consisting of titanium dioxide, copper oxide, zirconia, zinc oxide, silver oxide, and mixtures thereof, and a binder which comprises high density polyethylene, and wherein at least a portion of the metal oxide is in contact with the water.

19. The method of claim 1, further comprising at least partially immersing in the water one or more metals in the same vessel or conduit.

20. The method of claim 19, wherein the metal is in the form of metallic powder or metallic wires.

21. The method of claim 19, wherein the metal comprises zinc.

22. The method of claim 19, wherein the metal comprises copper.

23. The method of claim 19, wherein the metal comprises an alloy of zinc or copper or both.

24. The method of claim 19, wherein the metal comprises an alloy of copper and zinc.

25. The method of claim 19, wherein the metal comprises metal wire in the form of a metal wool.

26. The method of claim 25, wherein the metal wool comprises an alloy of zinc and copper in a ratio ranging between about 70:30 to about 50:50.

27. The method of claim 1, wherein the temperature inside the equipment is between about 34° and about 38° F.

28. The method of claim 27, wherein the temperature inside the equipment is between about 36° and about 38° F.

29. The method of claim 1, wherein the pH of the water inside the equipment is between about 5.5 and about 8.5.

30. The method of claim 18, wherein the metal oxide is fumed.

31. A method of reducing the growth of microorganisms in an ice maker, comprising at least partially immersing in water contained in a water reservoir of the ice machine,
- a) an antimicrobial composition comprising from about 2% to about 75% wt of a metal oxide mixture selected from the group consisting of fumed titanium dioxide, fumed copper oxide, fumed zinc oxide, and mixtures thereof; from about 10% to about 25% of a binder; and from about 10% to about 70% of a substrate selected from the group consisting of carbon, alumina, or silicates, wherein at least a portion of the metal oxide is in contact with the water; and
- b) a metal alloy of copper and zinc in the form of a metal wool.

32. A method of reducing the growth of microorganisms in water processing or storage equipment comprising:
- at least partially immersing a material comprising an antimicrobial composition in the water in a vessel or conduit inside the equipment, wherein the antimicrobial composition comprises an antimicrobial-effective amount of at least one metal oxide selected from the group consisting of titanium dioxide, copper oxide, zirconia, zinc oxide, silver oxide, and mixtures thereof, and a binder, and wherein at least a portion of the metal oxide is in contact with the water; and
- at least partially immersing in the water one or more metals in the form of a metal wool in the same vessel or conduit.

* * * * *